(12) United States Patent
Peters et al.

(10) Patent No.: US 9,285,137 B2
(45) Date of Patent: Mar. 15, 2016

(54) ARRANGEMENT FOR HEATING A MEDICAL FLUID, MEDICAL FUNCTIONAL DEVICE, MEDICAL TREATMENT APPARATUS AND METHOD

(75) Inventors: Arne Peters, Bad Homburg (DE); Michael Herrenbauer, Neu-Anspach (DE); Stefan Kreber, Saarbruecken (DE); Christoph Wiktor, Gelnhausen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 320 days.

(21) Appl. No.: 13/810,133

(22) PCT Filed: Jul. 18, 2011

(86) PCT No.: PCT/EP2011/003580
§ 371 (c)(1),
(2), (4) Date: Feb. 7, 2013

(87) PCT Pub. No.: WO2012/019693
PCT Pub. Date: Feb. 16, 2012

(65) Prior Publication Data
US 2013/0136431 A1   May 30, 2013

(30) Foreign Application Priority Data
Jul. 20, 2010   (DE) .......................... 10 2010 031 802

(51) Int. Cl.
| | |
|---|---|
| *F24C 1/00* | (2006.01) |
| *A61F 7/00* | (2006.01) |
| *F24H 9/00* | (2006.01) |
| *A61M 1/14* | (2006.01) |
| *F25B 21/04* | (2006.01) |

(52) U.S. Cl.
CPC . *F24H 9/00* (2013.01); *A61M 1/14* (2013.01); *F25B 21/04* (2013.01); *A61M 2205/127* (2013.01); *A61M 2205/366* (2013.01); *A61M 2205/3666* (2013.01); *A61M 2205/3673* (2013.01)

(58) Field of Classification Search
None
See application file for complete search history.

(56) References Cited

U.S. PATENT DOCUMENTS

| | | |
|---|---|---|
| 3,206,937 A | 9/1965 | Walisch et al. |
| 3,262,492 A | 7/1966 | Meenan |
| 3,399,536 A | 9/1968 | Walz |
| 4,210,153 A | 7/1980 | Fehlau et al. |
| 6,743,201 B1 | 6/2004 | Donig et al. |
| 7,648,475 B2 | 1/2010 | De Cicco et al. |
| 2004/0079089 A1 | 4/2004 | Wallach |
| 2006/0173396 A1 | 8/2006 | Hatamian |
| 2008/0097562 A1 | 4/2008 | Tan |

FOREIGN PATENT DOCUMENTS

| | | |
|---|---|---|
| EP | 0 956 876 B1 | 11/1999 |
| FR | 2 938 440 A1 | 5/2010 |
| WO | 03/055543 A1 | 7/2003 |

OTHER PUBLICATIONS

International Search Report from PCT/EP2011/003580 mailed on Nov. 15, 2011.

*Primary Examiner* — Thor Campbell
(74) *Attorney, Agent, or Firm* — Kenyon & Kenyon LLP (57) ABSTRACT

An arrangement for heating a medical fluid includes at least one electrically operated first heating device including at least one first warm section heating during operation of the first heating device and at least one first cold section cooling during operation of the first heating device; a first area for receiving the medical fluid to be heated, in which the first area is in heat exchange relation with the first warm section of the first heating device; and a second area that is in heat exchange relation with the first cold section of the first heating device. A medical functional device, a medical treatment apparatus as well as methods for setting and/or maintaining the temperature of a medical fluid are also described.

17 Claims, 6 Drawing Sheets

ARRANGEMENT FOR HEATING A MEDICAL FLUID, MEDICAL FUNCTIONAL DEVICE, MEDICAL TREATMENT APPARATUS AND METHOD

CROSS REFERENCE TO RELATED APPLICATIONS

The present application is the national stage entry of International Patent Application No. PCT/EP2011/003580, filed on Jul. 18, 2011, which claims priority to Application No. DE 10 2010 031 802.7, filed in the Federal Republic of Germany on Jul. 20, 2010.

FIELD OF INVENTION

The present invention relates to an arrangement. It further relates to a medical functional device, a medical treatment apparatus and a method.

BACKGROUND INFORMATION

In medical practice, it is sometimes necessary to set and/or maintain the temperature of extracorporeally present physiological liquids. Therefore, it is, for example, usual during a dialysis to warm or heat, respectively, dialysis liquid and/or blood, in particular after having passed through the dialysis filter.

SUMMARY

An object of the present invention is to propose a further arrangement for setting and/or maintaining the temperature of medical fluids. Furthermore, an appropriate method is proposed.

All or some of the advantages achievable by means of the arrangement according to the present invention may undiminishedly also be obtained by means of the medical functional device, the medical treatment apparatus and/or the method.

According to the present invention, an arrangement suited for warming or heating, respectively, a medical fluid is proposed.

In some exemplary embodiments of the present invention, the arrangement according to the present invention can be intended or provided and/or used for warming or heating, respectively, the medical fluid.

The arrangement according to the present invention comprises at least one electrically operated first heating device. The first heating device comprises at least one first warm section which heats during operation of the first heating device and at least one first cold section which cools or cools down, respectively, during operation of the first heating device.

Furthermore, the arrangement according to the present invention comprises a first area that is suited and/or intended or provided for receiving the medical fluid to be heated. In certain exemplary embodiments of the present invention, the first area is in heat exchange relation with the first warm section of the first heating device. A second area of the arrangement according to the present invention is in heat exchange relation with the first cold section of the heating device.

In certain exemplary embodiments of the present invention, exactly the opposite hereof holds true: the first area is in heat exchange relation with the first cold section of the first heating device and the second area is in heat exchange relation with the first warm section of the first heating device.

The medical functional device according to the present invention comprises at least one arrangement according to the present invention.

The medical treatment apparatus according to the present invention comprises at least one arrangement according to the present invention or at least one medical functional device according to the present invention.

The method according to the present invention serves for setting and/or maintaining the temperature of a medical fluid and comprises using an arrangement according to the present invention.

The term "warm section" as used herein refers to a section or segment or portion, respectively, of the first heating device having a higher temperature as compared to the "cold section" of the first heating device; correspondingly, the cold section has a lower temperature than the warm section.

In some exemplary embodiments according to the present invention, a "warm section" as used herein refers to a section of the heating device that heats due to supplying electrical energy.

In certain exemplary embodiments according to the present invention, a "cold section" as used herein refers to a section of the heating device that cools or cools down, respectively, due to supplying electrical energy.

According to the present invention, a "section" can be understood as a part or portion, respectively, of a surface or plane, respectively, or as the entire surface or plane, respectively, for example, a surface or plane provided or intended for receiving heat, transferring heat and/or emitting or outputting, respectively, heat.

In particular, in some exemplary embodiments according to the present invention, a warm section can be understood as a section that is intended or provided for warming or heating, respectively—or transiently or temporarily cooling or cooling down, respectively—a fluid in a targeted manner.

The terms "warm section" and "cold section" are exclusively to be understood in relation to each other. Thus, no conclusions should be drawn regarding absolute temperature values of the warm section and the cold section.

The term "heat exchange relation" as used herein refers to a spatial relation between two structures allowing an exchange or a transfer of heat—or cold as well—between the two structures. Thereby, the heat transfer can be intended and/or occur in any way known, e.g., by means of convection, heat transfer, heat radiation.

In some exemplary embodiments according to the present invention, the "heat exchange relation" is accompanied by a corresponding structural design or construction, respectively.

The term "area" as used herein generally refers to a section or segment or portion, respectively, a space, a surface or plane, respectively, or the like, that is able to enter or undergo a heat exchange relation with either the warm section or the cold section of a heating device or that is suited and provided or intended for a heat exchange with the warm section or the cold section of the heating device.

In some exemplary embodiments of the present invention, the first and/or the second area may be a closed area such as, e.g., a tubing section, a line, or the like, as well as sections or portions thereof. In other exemplary embodiments, the first and/or the second area may be an open or semi-open area or an area that is flown through in a directed or an undirected manner. The first and/or the second area may be a limited area. The first and/or the second area may be an area present in the collateral, immediate or direct surroundings or vicinity, respectively, of the arrangement according to the present invention.

In certain exemplary embodiments of the present invention, the second area is a hard or solid part such as a heat sink or a heat dissipater, a cooling fin, a thermal bridge, or the like.

In certain exemplary embodiments of the present invention, the second area is provided or intended for receiving a second fluid.

In some exemplary embodiments of the present invention, the first area is part of a fluid circuit. In certain exemplary embodiments, the first area is a fluid area.

In certain exemplary embodiments of the present invention, the second area is part of a fluid circuit. In certain exemplary embodiments, the second area is a fluid area.

In certain exemplary embodiments of the present invention, the first area and the second area are part—of the same; in some exemplary embodiments, parts of different, respectively—fluid circuits.

Thereby, a fluid circuit is in some exemplary embodiments according to the present invention a closed guidance or channel, respectively, of the fluid. In certain exemplary embodiments according to the present invention, the fluid circuit is, however, not closed; in those exemplary embodiments, e.g., fluid flows from a source through the fluid circuit in order to be discarded after its use without being returned back to the source. Here, the term "circuit" is used for those exemplary embodiments as well.

In certain exemplary embodiments of the present invention, the first area is part of a fluid circuit, the second area is not part of a fluid circuit, or vice versa.

In certain exemplary embodiments of the present invention, the first area and/or the second area are designed or embodied for conducting or directing a fluid in a targeted manner.

In some exemplary embodiments of the present invention, the area may be a line. The fluid may be guided or conducted, respectively, or directed within the line.

The line may be defined line. The line may be a part or constituent, respectively, of the arrangement according to the present invention.

The line may be an external device, relative to the arrangement according to the present invention. The line can be connectable or connected with the arrangement according to the present invention. The line may be part of an (optionally superior) fluid circuit.

The term "heating device" as used herein refers to a device suited and/or provided or intended for warming or heating, respectively, a medical fluid.

In certain exemplary embodiments, the arrangement according to the present invention is suited and/or provided or intended for cooling or cooling down, respectively, the medical fluid.

In certain exemplary embodiments of the present invention, the arrangement according to the present invention is provided for heating the medical fluid in a first time interval and provided for cooling the medical fluid in a second time interval differing from the first time interval.

In some exemplary embodiments, the arrangement according to the present invention comprises a device suited and/or provided or intended for at least transiently or temporarily, respectively, prompting cooling the medical fluid by means of the first warm section instead of heating the medical fluid by means of the warm section. This can, e.g., be induced or initiated, respectively, by reversing a current supply for the electrically operated first heating device.

Such a device can be a switch, e.g., a switch or diverter, respectively, in an electric circuit into which the first heating device is integrated for the purpose of current supply.

The first heating device may be or comprise a thermocouple or thermal element.

In certain exemplary embodiments of the present invention, the first heating device is or comprises a Peltier element. In some exemplary embodiments of the present invention, the first heating device comprises a plurality of Peltier elements.

In certain exemplary embodiments of the present invention, the arrangement comprises an electrically operated second heating device comprising at least one second warm section which heats during operation of the second heating device and at least one second cold section which cools during operation of the second heating device.

Thereby, in some exemplary embodiments according to the present invention, heating and cooling are each effected or prompted or induced, respectively, by activation or by current supply; however, in certain exemplary embodiments according to the present invention, they are at least resulting therefrom.

In certain exemplary embodiments, the second heating device is suited and/or provided or intended to warm or heat, respectively, a fluid, in particular the medical fluid, or to contribute to warming or heating, respectively, the latter.

All exemplary embodiments described in connection with the first heating device may in certain exemplary embodiments also apply for the second heating device, and vice versa.

In exemplary embodiments, in which the arrangement according to the present invention comprises two heating devices, the warm section being in heat exchange relation with the first area may be the first warm section of the first heating device. The cold section being in heat exchange relation with the second area may be the second cold section of the second heating device. In other exemplary embodiments of the present invention, exactly the opposite may be true.

In certain exemplary embodiments of the present invention, the second area is connectable or connected with the first cold section of the first heating device for warming or heating, respectively, the first cold section or the second cold section. In some exemplary embodiments of the present invention, the second area is connectable or connected with the second cold section of the second heating device.

According to the present invention, the heat exchange relation can be a connection. The connection can be a physical connection. In certain exemplary embodiments of the present invention, the second area is in physical contact with the cold section to be heated.

Heating the first cold section or the second cold section may particularly be achieved by transferring heat from the second fluid of the second area onto the corresponding cold section.

The second fluid is a liquid or a gas that is provided for emitting or transferring heat (from or by means of the second area) to a cold section (the first cold section of the first heating device or the second cold section of the second heating device).

In certain exemplary embodiments of the present invention, the medical fluid and the second fluid are substantially identical.

The medical fluid may be a medical liquid such as blood, in particular an extracorporeal liquid such as blood, dialysis liquid, substitute liquid, drug solutions, and the like, combinations or mixtures thereof.

In certain exemplary embodiments of the present invention, the medical fluid is dialysis liquid or extracorporeal blood.

In certain exemplary embodiments of the present invention, the arrangement according to the present invention comprises at least one heat transfer fluid circuit comprising a first and a second heat transfer area.

The heat transfer fluid circuit is preferably a closed fluid circuit, e.g., a self-contained fluid circuit.

The first heat transfer area and the second heat transfer area are provided or intended for receiving a heat transfer fluid.

The term "heat transfer fluid" as used herein refers to a fluid suited for transferring heat. The heat transfer fluid can be intended or provided for transferring heat.

Examples of appropriate heat transfer fluids include water, oil, and the like.

In the heat transfer fluid circuit, the heat transfer fluid may circulate automatically or supportingly or exclusively be conveyed by means of (at least one) appropriate device such as a conveying device, provided or intended therefor.

In certain exemplary embodiments of the arrangement according to the present invention, the heat transfer fluid circuit is arranged between the first area and the second area.

The heat transfer fluid circuit can be arranged between the first area and the second area such that the first warm section of the first heating device is in heat exchange relation with the first area; the first cold section of the first heating device is in heat transfer relation with the first heat transfer area; the second warm section of the second heating device is in heat exchange relation with the second heat transfer area; and the second cold section of the second heating device is in heat exchange relation with the second area.

In those exemplary embodiments, the heat transfer fluid can be used as a means for transferring heat (from the second area across the heat transfer fluid circuit) onto the first cold section.

The use of a heat transfer fluid circuit between the first and the second area may particularly be of advantage if the medical fluid and the second fluid shall be separated physically or spatially, respectively, from each other hereby. This excludes a contamination or impurity risk for the medical fluid due to the second fluid.

In certain exemplary embodiments of the present invention, the arrangement according to the present invention is designed or embodied as a reusable unit. In those exemplary embodiments, the arrangement according to the present invention is provided for multiple uses.

The arrangement according to the present invention may comprise firmly installed or fixed lines, in particular lines to be used multiply, or non-firmly installed or unfixed lines or may be connected with firmly installed or fixed lines or with non-firmly installed or unfixed lines. In certain exemplary embodiments, the arrangement according to the present invention may be connected with lines that are firmly installed or fixed at or on, respectively, a medical treatment apparatus.

In certain other exemplary embodiments of the present invention, the arrangement according to the present invention is designed or embodied as a single-use article or a disposable or a one-way article. In those exemplary embodiments, it is intended to use the arrangement according to the present invention only once and to dispose the latter after its one-time or single use.

The arrangement according to the present invention can be designed or embodied as a part of a medical functional device.

In some exemplary embodiments, the arrangement according to the present invention is integrally designed or embodied with a medical functional device or integrated within a medical functional device, respectively.

In certain exemplary embodiments, the medical functional device is designed or embodied as a single-use article or a disposable or a one-way article. In certain exemplary embodiments, the medical functional device is a (disposable) blood cassette.

The medical functional device may be a cassette of the sleepsafe cassette type made by Fresenius Medical Care (Bad Homburg, Germany).

The sleep safe PD cycler is an automated peritoneal cycler for home or clinical use. The pump action or effect, respectively, is ensured by a hydraulically operated membrane piston pump.

The sleep safe set is a single-use article comprising semi-circular chambers in which the hydraulic medium either pushes the solution through a membrane out of the chamber or pulls the solution into the chamber. An integrated heating device heats the dialysis solution prior to its infusion into the patient. An automatic connection system connects the solution bags with the tubing set. Different pressure sensors monitor the pressures in the system. The system is controlled and monitored by a microprocessor. A processor represents an independent safety system.

A detailed description of a sleepsafe cassette may be derived from the European Patent No. EP 0 956 876 B1, the contents of which are fully incorporated herein by reference thereto.

The medical functional device according to the present invention can comprise at least one fluid circuit, for example, two fluid circuits, for example for (fresh and used) dialysis liquids or for extracorporeal blood (in front of and behind a treatment device such as a blood treatment filter).

The arrangement according to the present invention may be functionally coupable or coupled to a medical treatment apparatus.

Appropriate medical treatment apparatuses may include blood treatment apparatuses, in particular dialysis apparatuses, such as an acute dialysis apparatus, and the like.

The method according to the present invention can be used for warming or heating, respectively, a medical fluid.

By using the arrangement according to the present invention, this may in certain exemplary embodiments of the method according to the present invention include to firstly introduce a medical fluid into a first area.

The medical fluid is heated in the first area by means of the first heating device by transferring heat from the first warm section of the first heating device onto the first area.

In certain exemplary embodiments of the present invention, it is intended to heat the first cold section of the first heating device or the second cold section of the second heating device by transferring heat of the second fluid of the second area onto the first cold section of the first heating device or the second cold section of the second heating device.

In other exemplary embodiments of the method according to the present invention, particularly an arrangement according to the present invention comprising two heating devices and a heat transfer fluid circuit is used.

The heat transfer fluid circuit can be embodied or designed and/or arranged as stated above in this regard.

In those exemplary embodiments of the method according to the present invention, the method can comprise heating the second cold section of the second heating device by transferring heat of the second fluid of the second area onto the second cold section of the second heating device. It can further comprise heating the heat transfer fluid in the second heat transfer area by means of the second heating device by transferring heat from the second warm section of the second heating device onto the second heat transfer area. Moreover, it may comprise transferring heat of the heat transfer fluid of the first heat transfer area onto the first cold section of the first heating device.

An exchange of heat or a transfer of heat of the heat transfer fluid from the second heat transfer area onto the first heat transfer area can be achieved by directing or conducting the heat transfer fluid within an interior of the heat transfer fluid circuit.

Thereby, in some exemplary embodiments of the present invention, the heat transfer fluid can automatically move through an interior of the heat transfer fluid circuit. In some exemplary embodiments, an appropriate device such as a conveying device for conveying the heat transfer fluid within the heat transfer fluid circuit, may be used.

In certain exemplary embodiments, the method according to the present invention serves for heating a medical fluid in a first time interval and for cooling the medical fluid in a second time interval differing from the first time interval.

In those exemplary embodiments of the method according to the present invention, it can be intended to heat the medical fluid in the first area by means of the first heating device within the first time interval. Alternatively, e.g., by changing the current supply (or by reversing the current flow direction) for the electrically operated first and/or the second heating device, it can be effected that the medical fluid is not heated in the first area by means of the first warm section of the first heating device, but is cooled by transferring cold from the first warm section of the first heating device.

In some exemplary embodiments, changing the current supply may be achieved by using a switch provided in an electric circuit for supplying/current supply to the first heating device and/or the second heating device.

Exemplary embodiments of the present invention can comprise one or more of the following advantages.

The present invention provides an arrangement that allows using a second fluid, for example, in particular waste heat of a treatment system such as, for example, of actuator technology, sensor technology and/or electronic components, for heating certain segments, sections or portions, respectively, of heating devices such as, e.g., cold sections of Peltier elements, or the like, during heating of a medical fluid in a simple and technically uncomplicated manner.

This way, it may in certain exemplary embodiments of the present invention advantageously be possible to omit heaters for heating blood and/or dialysate and to thus advantageously avoid a higher energy demand of the dialysis machines.

This can particularly advantageously contribute to avoiding higher temperatures in the machine interior.

By using waste heat, there may advantageously be achieved a high energy efficiency of the system in certain exemplary embodiments of the present invention. Thus, the second fluid used for heating the cold section of the heating device may in certain exemplary embodiments of the present invention conduct waste heat of electronic components, e.g., the waste heat of machine elements present in dialysis machines as well as the waste heat of used dialysate.

The energy efficiency of the system may advantageously be further enhanced by an active heat exchange between fresh and used dialysate.

In certain exemplary embodiments, using such waste heat may advantageously contribute to reducing or even preventing a discarding or discharging of the waste heat without taking benefit thereof, or even applying additional energy for a required discharging of the waste heat (e.g., by using ventilators, fans, corresponding constructional measures, and the like).

Additionally, in certain exemplary embodiments of the present invention, it may advantageously be possible to omit large heat exchange surfaces or planes, respectively, at different components.

Furthermore, in certain exemplary embodiments of the present invention, it may advantageously be possible to provide a more compact and simpler construction of the machine by means of reduced heat exchange surfaces.

By omitting (one) ventilator(s) or correspondingly largely dimensioned ventilators, it may advantageously be possible to significantly reduce the sound level of the arrangement. Omitting (one) ventilator(s) usually having a high volume flow and a short durability may additionally advantageously contribute to saving cost and/or maintenance effort of the arrangement according to the present invention.

In certain exemplary arrangements according to the present invention, the amount of electrical energy may advantageously be reduced as compared to, for example, a classical resistance heating.

Furthermore, in certain exemplary embodiments of the present invention, by using the arrangement according to the present invention, it may be possible to use the amount of heat present in a used dialysis liquid profitably in an advantageously simple manner. Thus, in some exemplary embodiments according to the present invention, an elaborate recovering by means of space requiring heat exchanges or even a loss by discarding the dialysis liquid can be avoided. In particular the possible gain of construction space, but also further advantages can be of advantage in acute dialysis systems.

In certain exemplary embodiments of the present invention, by supplying or transferring, respectively, heat or heat energy, respectively, to the cold section of a heating device, it can advantageously be possible to reduce a temperature difference between the cold section and the warm section of the heating device. Thereby, it may advantageously be possible to reduce a loss of heat of a treatment system.

Moreover, it can advantageously be possible to achieve lower temperatures in the machine in general.

By means of the arrangement according to the present invention, a temperature difference between the cold section and the warm section of the heating device can in certain exemplary embodiments of the present invention advantageously be reduced such that a loss of heat or loss of heat energy, respectively, due to a heat flow from the warm section to the cold section that may particularly be generated in case of relatively high temperature differences, may advantageously be avoided.

The degree of efficiency of the arrangement according to the present invention and/or of a treatment system can thus be improved or even optimized. Additionally, it may advantageously be possible to reduce the current consumption.

This can be of particular advantage in treatment systems in which large amounts of physiological liquids are to be heated. Examples include blood treatment systems such as dialysis apparatuses and the like, in which flow rates of 500 ml/min (or more) of the dialysis liquid circuit may occur.

By means of the present invention, it may advantageously be possible to sufficiently heat also larger or large amounts of the medical fluids to be infused into the patient and to thus advantageously avoid a cooling off of the patient.

By using one or more Peltier elements or certain other elements in which current is used for generating thermal energy, it may in certain exemplary embodiments of the present invention advantageously be possible in a simple and uncomplicated manner to select, alternate, reverse or switch between heating and cooling of the medical fluid, the temperature of which shall be set and/or maintained, by simply reversing the current supply. In some exemplary embodiments of the present invention, it may hereby advantageously be possible, for example, to transiently draw energy from a dialysis liquid circuit and to thus advantageously prevent an overheating of the liquid and/or the heating device as well as overheating at the interfaces in case of, e.g., a stop of the dialysis liquid circuit. This may be of particular advantage in situations of a transient stop of the fluid, e.g., of the dialysis liquid or of the blood, in the first area in which heating is not required and overheating may be imminent. According to the present invention, corresponding temperature sensors, probes and/or controllers may be provided.

Due to their compact construction and/or their compact dimensions, Peltier elements may advantageously be used in areas in which only little space is available such as, for example, on a blood cassette for dialysis.

This can be of particular advantage in infusion technology and/or in dialysis technology in which compactness of therapy machines is required. Moreover, it may advantageously be possible to design fluid-conducting single-use articles compactly. In this way, a still increasing number of functions may be realized on one single-use article.

The arrangement according to the present invention may be used for heating dialysis liquid during an extracorporeal blood treatment. Such an exemplary use of the arrangement according to the present invention is described with respect to the appended drawings. However, the present invention is not limited thereto.

In the following, the present invention will be described exemplarily with respect to the appended drawings. In the drawings, identical reference numerals refer to same or identical elements.

DETAILED DESCRIPTION

Figure 1:
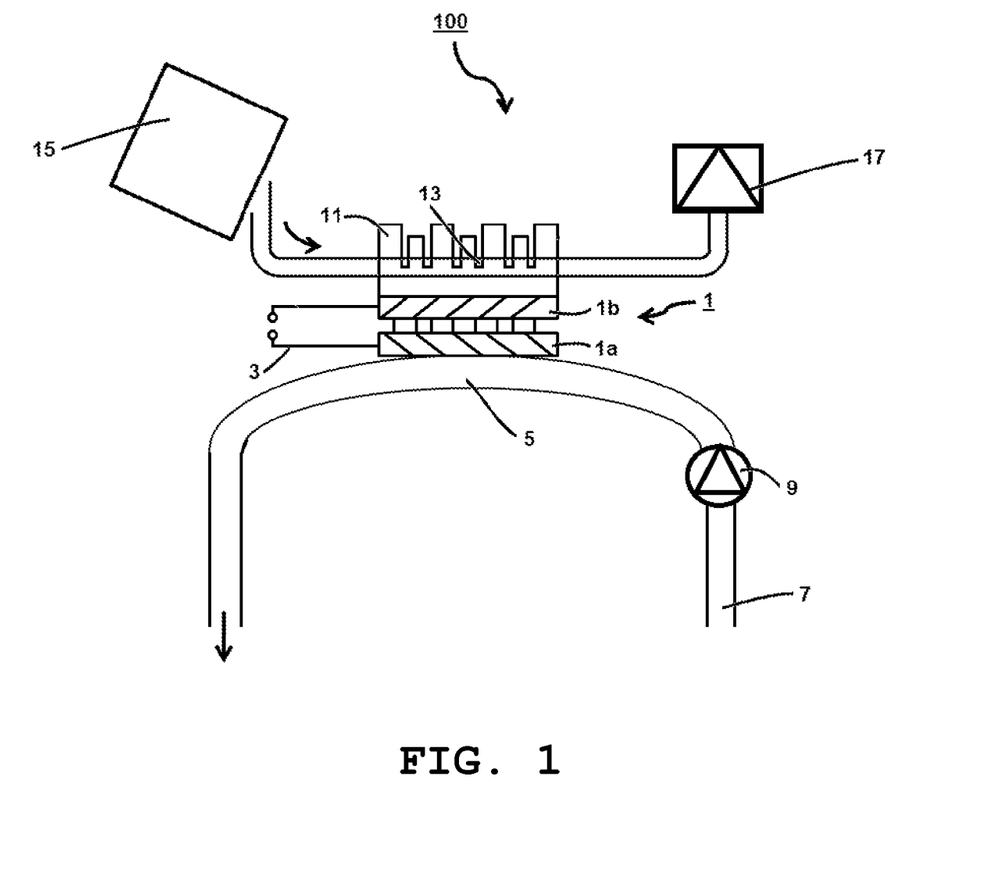
FIG. 1 shows an arrangement according to the present invention according to a first exemplary embodiment in a schematically simplified manner.

FIG. 1 shows an arrangement 100 according to the present invention in a first exemplary embodiment in a schematically simplified manner.

The arrangement 100 according to the present invention comprises a first heating device 1. The first heating device 1 may be or comprise a Peltier element.

The first heating device 1 comprises a first warm section 1*a* heating during operation of the first heating device 1 and a first cold section 1*b* cooling during operation of the first heating device 1.

For operating the first heating device 1, the latter is integrated into an electric circuit 3.

The arrangement 100 according to the present invention comprises a first area 5. The first area 5 is in heat exchange relation with the first warm section 1*a* of the first heating device 1.

In FIG. 1, the first area 5 is provided or intended for receiving dialysis liquid or dialysate, respectively, more precisely fresh dialysis liquid.

The fresh dialysis liquid may be present in a dialysis liquid line 7 comprising the first area 5 such as is exemplarily illustrated in FIG. 1. The dialysis liquid line 7 may be part of a dialysis liquid circuit—a closed or (semi-) open one, for example, being part of a superior dialysis liquid circuit.

Within the dialysis liquid line 7, a conveying device 9 for conveying the dialysis liquid within an interior of the dialysis liquid line 7 is provided.

The dialysis liquid can be conveyed in direction to a medical treatment device (not shown in FIG. 1) as is indicated by means of the arrow directed downwards (regarding the representation of FIG. 1). The medical treatment device can be a dialysis filter, e.g., of an acute dialysis system.

As shown in FIG. 1, a heat sink 11 is optionally provided at the cold section 1*b* of the first heating device 1. However, such a heat sink 11 is not mandatorily provided.

The heat sink 11 can be arranged in or at a second area 13 of the first heating device 1 as is exemplarily shown in FIG. 1. The heat sink 11 can enhance a cooling effect of the second area 13.

As exemplarily shown in FIG. 1, a second area 13 comprises a second fluid, for example, air. The air can be heated by means of waste heat of electronic components (summarized under reference numeral 15) of a medical treatment device.

Directing or conducting the second fluid is illustrated in FIG. 1 by means of the bent structure. The bent structure does not have to be a line. Generally, it does not have to be a closed space/area. A fan 17 can be used for directing the second fluid to the first cold section 1*b*. A flow direction of the second fluid is exemplarily shown by means of the bent arrow.

The second area 13 may rather be a substantially unlimited area, e.g., the atmosphere (at least the area in the immediate surroundings of the first cold section 1*b*).

The second fluid can transfer heat energy to or onto, respectively, the first cold section 1*b* of the first heating device 1.

Optionally after having passed the second area 13, residual heat of the second fluid that is still present may be removed by means of the fan 17.

Figure 2:
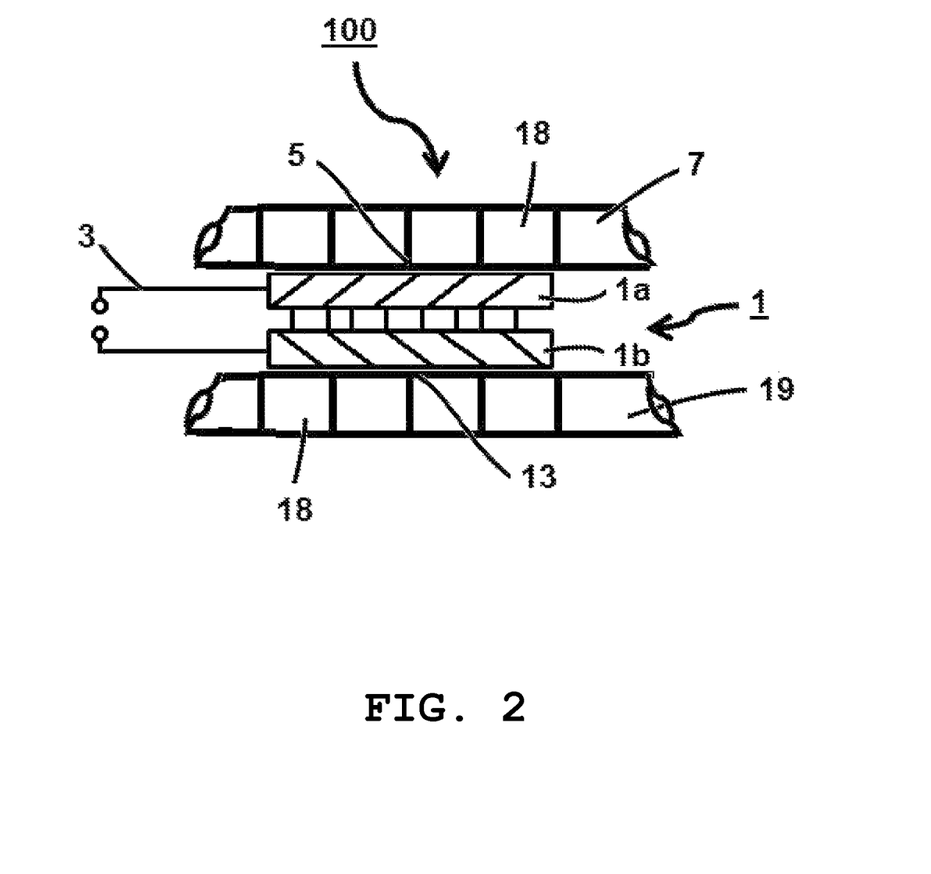
FIG. 2 shows an arrangement according to the present invention according to a second exemplary embodiment in a schematically simplified manner.

FIG. 2 shows an arrangement 100 according to the present invention in a second exemplary embodiment in a schematically simplified manner.

The arrangement 100 according to the present invention may be part of a medical functional device.

Such a medical functional device can thereby comprise one or more arrangements 100 according to the present invention. The medical functional device may comprise at least two fluid circuits, segments, sections or portions, respectively, thereof, for example, one for fresh and one for used dialysis liquid.

Appropriate fluid circuits may be arranged in meander form on or in, respectively, the medical functional device. An exemplary meander structure 18 is shown.

An appropriate medical functional device can be a cassette, in particular a blood cassette.

As shown in FIG. 2, a dialysis liquid line 19 for used dialysis liquid is arranged such that a second area 13 of the dialysis liquid line 19 is in appropriate heat exchange relation with the first cold section 1b of the first heating device 1.

In the example of FIG. 2, the second fluid is substantially or exclusively used dialysate.

The dialysis liquid line 7 substantially contains fresh dialysis liquid.

The dialysis liquid line 7 comprises the first area 5 that is in appropriate heat exchange relation with the first warm section 1a of the first heating device 1.

During operation of the first heating device 1, heat is "pumped" or—generally spoken—transferred from the cold section 1b to the warm section by supplying electrical energy by means of the electric circuit 3.

At the same time, heat is drawn from the used dialysis liquid of the dialysis liquid line 19 and used for heating the first cold section 1b. A temperature difference between the cold section 1b and the warm section 1a can thus be advantageously reduced.

The arrangement 100 shown in FIG. 2 may in some exemplary embodiments be designed or embodied as single-use article. However, in other exemplary embodiments, it can also be used as a fixed hydraulic section of, e.g., a medical treatment apparatus.

Figure 3:
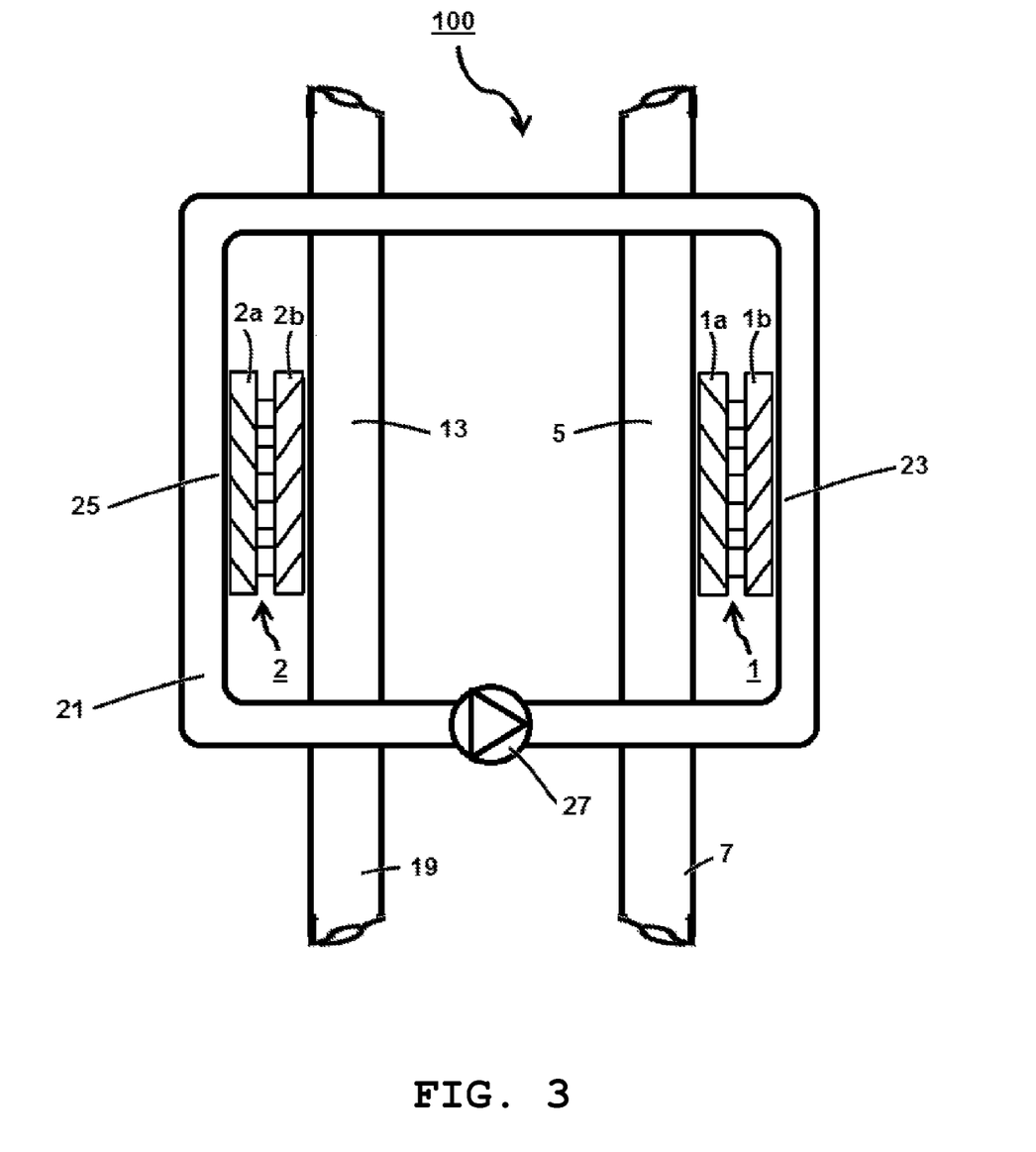
FIG. 3 shows an arrangement according to the present invention according to a third exemplary embodiment in a schematically simplified manner.

FIG. 3 shows an arrangement 100 according to the present invention in a third exemplary embodiment in a schematically simplified manner.

Instead of a direct heat transfer from the used to the fresh dialysis liquid as shown in FIG. 2, FIG. 3 illustrates a heat transfer by using a heat transfer fluid.

In some exemplary embodiments according to the present invention, the heat transfer fluid is specifically and/or exclusively intended or provided for transferring heat energy from a warm section of a heating device onto a cold section of another heating device.

The arrangement 100 according to the present invention comprises a heat transfer fluid circuit 21 comprising a heat transfer fluid, for example, oil, water, or the like.

The arrangement 100 according to the present invention furthermore comprises a second heating device 2. The second heating device 2 comprises a second warm section 2a heating during operation of the second heating device 2 and a second cold section 2b cooling during the operation of the second heating device 2.

The heat transfer fluid circuit 21 comprises a first heat transfer area 23 and a second heat transfer area 25.

The heat transfer fluid circuit 21 is arranged between the first area 5 and the second area 13 such that the first warm section 1a of the first heating device 1 is in heat exchange relation with the first area 5; the first cold section 1b of the first heating device 1 is in heat exchange relation with the first heat transfer area 23, the second warm section 2a of the second heating device 2 is in heat exchange relation with the second heat transfer area 25; and the second cold section 2b of the second heating device 2 is in heat transfer relation with the second area 13.

During operation for heating the medical fluid in the second area 13, in this arrangement 100, there is firstly transferred heat from the used dialysis liquid of the second area 13 or of the dialysis liquid line 19 for used dialysis liquid, respectively, onto the heat transfer fluid within the heat transfer fluid circuit 21 by means of the second heating device 2. Herefor, for example, the heat drawn from the used dialysis liquid is transferred from the second area 13 onto the second cold section 2b of the second heating device 2. Thereby, the second cold section 2b is advantageously heated.

Furthermore, by operating the second heating device 2, electrically generated heat is transferred from the second warm section 2a onto the second heat transfer area 25.

The heat transfer fluid heated thereby can be conveyed to the first cold section 1b of the first heating device 1 by means of an appropriate conveying device, for example, a pump 27 such as shown in FIG. 3.

At the first heating device 1, a heat transfer from the heat transfer fluid onto the first cold section 1b of the first heating device 1 takes place in the first heat transfer area 23. Thereby, the first cold section 1b is advantageously heated.

The fresh dialysis liquid of the dialysis liquid line 7 for fresh dialysis liquid is heated again by operating the first heating device 1 and by means of the heat transfer from the first warm section 1a onto the first area 5.

The arrangement described in FIG. 3 can in some exemplary embodiments offer the advantage of conducting fresh and used dialysis liquid in a spatially separated manner. However, heat of the used dialysis liquid otherwise discarded is used. Thus, a potential contamination risk may advantageously be prevented.

The arrangement 100 shown in FIG. 3 can be designed or embodied as a single-use article or as a—firmly installed or fixed, respectively—hydraulic segment, section or portion, respectively, provided or intended for multiple usage.

In FIGS. 2 and 3, the present invention has been described with respect to exemplary embodiments in which both the medical fluid and the second fluid are present as dialysis liquid. Still, the present invention may also be carried out in the same way using other fluids as is described with respect to FIG. 1. Appropriate examples include an arrangement in which, instead of dialysis liquid flows, heat is drawn from extracorporeal patient blood prior to conducting the same into a (blood treatment) filter and the said heat is supplied to the patient's blood before returning the blood back to the patient.

Figure 4A:
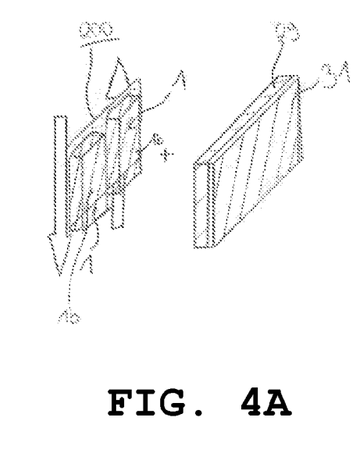
FIG. 4A shows an arrangement according to the present invention according to a fourth exemplary embodiment in a perspective view in a schematically simplified manner.

FIG. 4A shows in a perspective view an arrangement 100 according to the present invention according to a fourth exemplary embodiment in a schematically simplified manner, in which a heating device 1—here shown as a Peltier heating element—comprising a heat exchanging function is arranged planely at or on a single-use article 200.

It is intended to arrange a thermal bridge 29 comprising an insulation 31 at the cold section 1b of the heating devices 1.

Such an exemplary embodiment in which no heating surfaces (heating devices, Peltier elements) protrude out of the machine front of a treatment apparatus may provide several advantages. Those advantages include lower costs for the single-use article 200, a better handling, an easier construction, and the like.

Figure 4B:
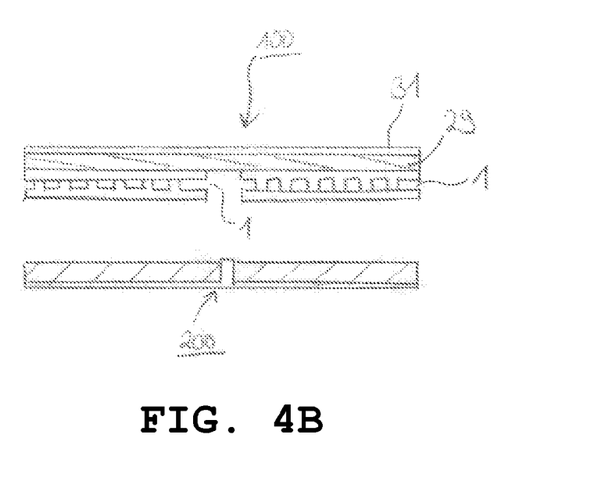
FIG. 4B shows the arrangement according to the present invention arranged at or on a functional device in a schematically simplified manner.

In the exemplary embodiments shown in FIGS. 4A and 4B, two heating devices 1 are connected via a thermal bridge 29 in order to transport heat from the used dialysate to the cold fresh dialysate. The block arrows of FIG. 4A correspondingly denote the flows of fresh and used dialysate along or over, respectively, the single-use article 200.

FIG. 4B shows an arrangement 100 at or on, respectively, a functional device, here the single-use article 200, in a schematically simplified manner.

For reasons of illustration, a gap is shown between the arrangement 100 and the single-use article 200.

Figure 5:
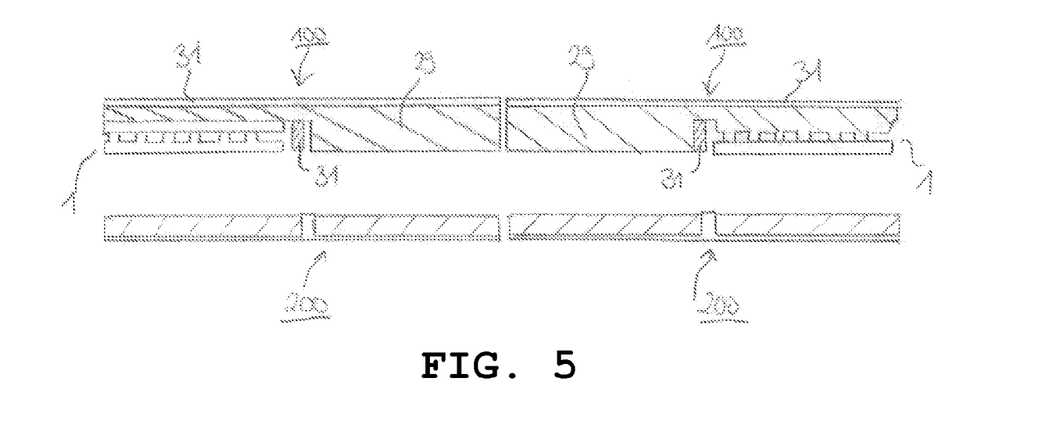
FIG. 5 shows an arrangement according to the present invention according to a fifth exemplary embodiment in a schematically simplified manner.

FIG. 5 shows an arrangement 100 according to the present invention according to a fifth exemplary embodiment in which a heating device 1 is again planely arranged at the single-use article 200 during operation, in a schematically simplified manner. However, merely for better understanding, a gap between single-use article 200 and heating device 1 is also shown in FIG. 5.

The function of a plane active heat exchanger may be realized by means of a Peltier element. In such an exemplary embodiment, the thermal bridge 29 may at the same time or likewise become the cooling or the heating side.

In FIGS. 6 to 9, the heating device is part of the functional device, respectively. In the representations of FIGS. 6 to 9, it is not shown, respectively.

Figure 6:
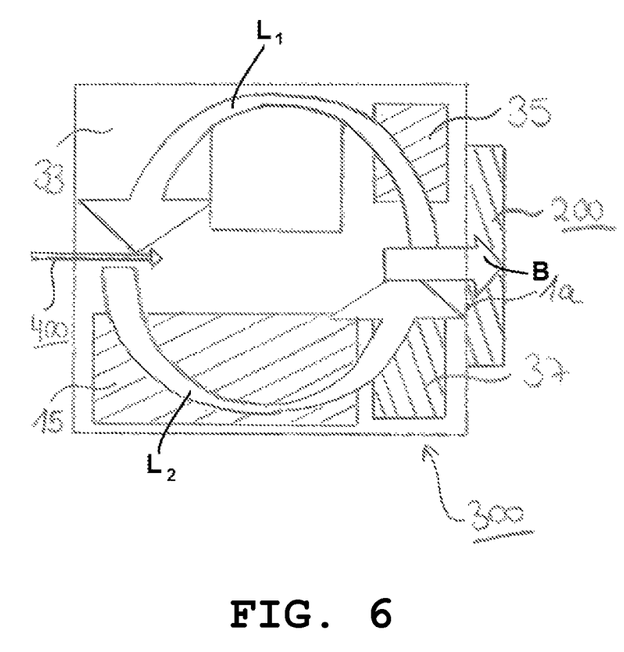
FIG. 6 shows a heat management by means of the arrangement according to the present invention in a schematically simplified manner.

FIG. 6 shows a heat management of a treatment apparatus 300 by means of the arrangement 100 according to the present invention in a schematically simplified manner.

In the exemplary embodiment shown in FIG. 6, heating the cold section of the heating device is achieved by means of an air flow 400 (fan)—in particular one that is conducted in a targeted manner.

The heating device draws heat from a machine interior 33 of the treatment apparatus 300 via the warm section 1a of the heating device and transfers the heat onto the single-use article 200 in which the liquid is heated. The heat transport is illustrated by means of the block arrow B in direction to the single-use article 200.

By means of the circulation (represented by means of the bent arrows $L_2$ and $L_2$) of air within the treatment apparatus 300, the air exchange between the waste heat of the electronic components 15, the sensor technology 35 and/or the actuator technology 37 present and the heating device can be optimized.

Figure 7:
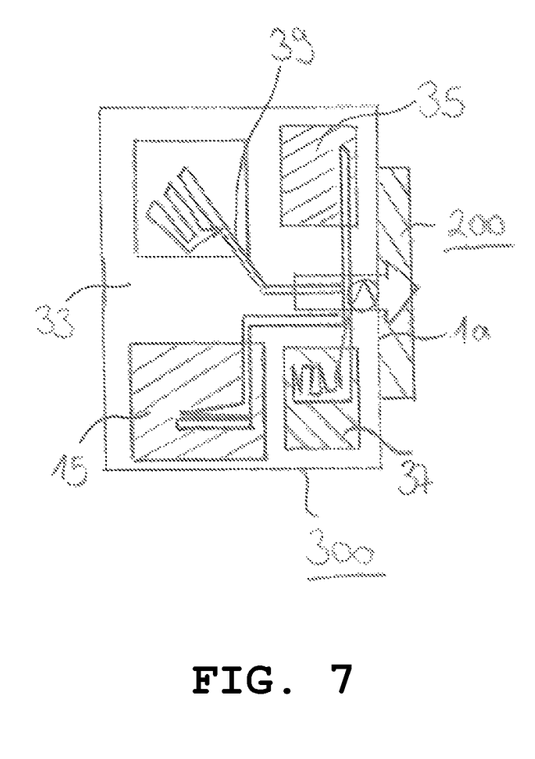
FIG. 7 shows a further heat management by means of the arrangement according to the present invention.

FIG. 7 shows a further heat management by means of the arrangement 100 according to the present invention in a treatment apparatus 300.

In the exemplary embodiment shown in FIG. 7, heating the cold section of the heating device is achieved by means of a liquid—in particular a liquid that is conducted in a targeted manner.

For dissipating the waste heat of the electronic components 15, the sensor technology 35 and/or the actuator technology 37, a fluid system 39 is used that may comprise manifold or distributor tubes, heat exchangers, liquid and/or one or more pumps.

In such an exemplary embodiment, the treatment apparatus 300 may advantageously be dimensioned even more compactly. Using a liquid as the heat exchanger or heat exchange medium, respectively, may advantageously optimize the heat transfers and/or the amount of heat transferred.

Figure 8:
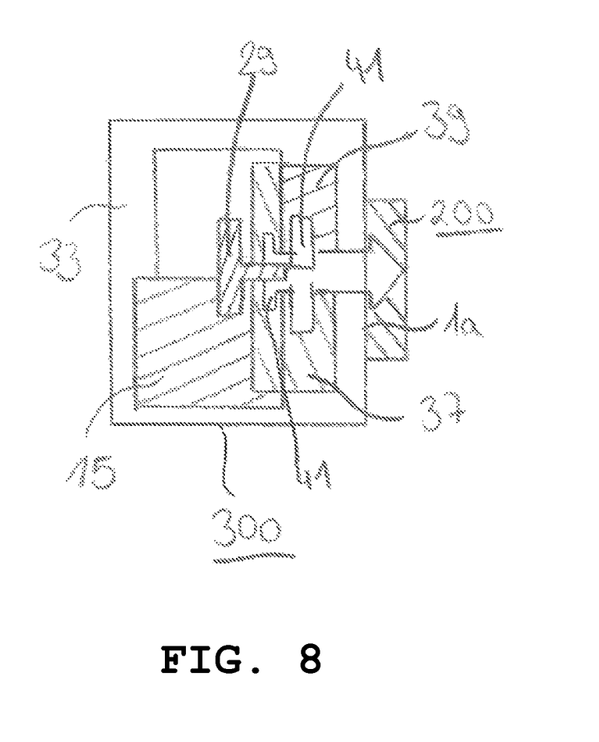
FIG. 8 shows a further heat management by means of the arrangement according to the present invention.

FIG. 8 shows a further heat management by means of the arrangement 100 according to the present invention in or at a treatment apparatus 300.

In the exemplary embodiment shown in FIG. 8, the heat transfer is achieved by means of solid materials such as a thermal bridge 29. In those exemplary embodiments, using a fluid for heat transfer may be omitted. However, the latter can be provided additionally as well as a heat transfer by means of air—in particular air conducted in a targeted manner.

The elements to be cooled are connected with the heating device by at least one dissipater or cooling block 41. For a lower thermal output, a heat conducting film can be used for the dissipater 41; for high heat emissions, preferably aluminum, copper and/or ceramics such as aluminum nitride (AlN), and the like, can be used.

Figure 9:
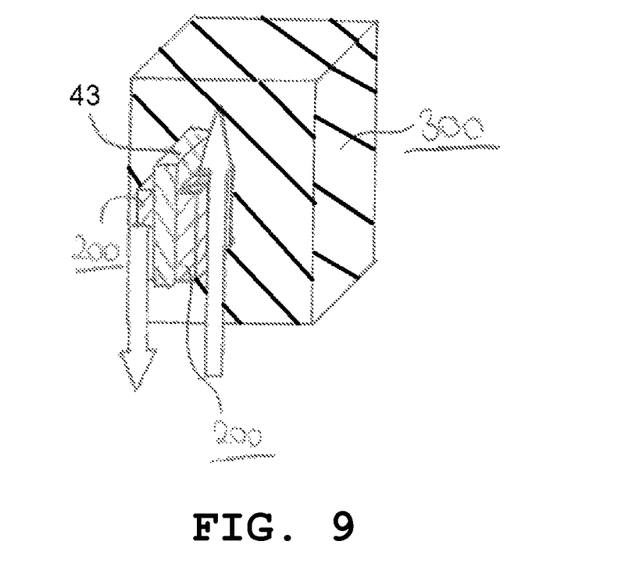
FIG. 9 shows an arrangement according to the present invention arranged at or on a treatment apparatus in a schematically simplified manner.

FIG. 9 shows an arrangement 100 according to the present invention at or on, respectively, a treatment apparatus 300 in a schematically simplified manner.

In the exemplary embodiment shown in FIG. 9, two heating devices are each arranged in a single-use article 200 at the right and at the left side, related to the representation of FIG. 9, of a cooling fin 43.

The cooling fin 43 is decoupled from the treatment apparatus 300 or an interior of the treatment apparatus 300, respectively. The cooling fin 43 is arranged at the machine front of the treatment apparatus 300 such that it projects or protrudes, respectively, from the treatment apparatus 300.

Used dialysate (block arrow downwards) and fresh dialysate (block arrow upwards) are conducted along or over, respectively, the single-use articles 200.

Used dialysate emits heat to the cold section of the heating device in the left single-use article. The warm section of the said heating device emits heat to the cooling fin 43. The cooling fin 43 emits heat to the cold section of the heating device in the right single-use article for the fresh dialysate. The warm section of this heating device is used for heating the fresh dialysate such that warm fresh dialysate is conducted along or over, respectively, the blood.

The exemplary embodiment shown in FIG. 9 can provide the advantage that the cooling fin 43 is independent from the machine interior of the treatment apparatus 300.

The invention claimed is:

1. An arrangement for heating a dialysis liquid during an extracorporeal blood treatment, comprising:
   at least one electrically operated first heating device comprising at least one first warm section configured to heat during operation of the first heating device, and at least one first cold section configured to cool during operation of the first heating device;
   a first area for receiving the dialysis liquid to be heated, wherein the first area is in heat exchange relation with the first warm section of the first heating device; and
   a second area for receiving used dialysate, wherein the second area is in heat exchange relation with the first cold section of the first heating device,
   wherein the first area and the second area are adapted such that heat is drawn from the used dialysate and transferred through the first cold section and through the first warm section to heat the dialysis liquid.

2. The arrangement according to claim 1, wherein at least one of the first area and the second area are configured for conducting or directing a fluid in a line in a targeted manner.

3. The arrangement according to claim 1, wherein the arrangement is configured for heating the dialysis liquid in a first time interval and configured for cooling the dialysis liquid in a second time interval differing from the first time interval.

4. The arrangement according to claim 3, further comprising:
   a device for at least transiently prompting cooling the dialysis liquid by the first warm section instead of heating the dialysis liquid by the first warm section by reversing a current supply for the electrically operated first heating device.

5. The arrangement according to claim 1, wherein the first heating device is or comprises at least one Peltier element.

6. The arrangement according to claim 1, further comprising:
   at least one electrically operated second heating device comprising at least one second warm section configured to heat during operation of the second heating device and at least one second cold section configured to cool during operation of the second heating device;
   wherein the first warm section of the first heating device is in heat exchange relation with the first area, and the second cold section of the second heating device is in heat exchange relation with the second area.

7. The arrangement according to claim 6, wherein the second area is connected with the first cold section of the first heating device or with the second cold section of the second heating device for heating the first cold section or the second cold section.

8. The arrangement according to claim 6, further comprising:
at least one heat transfer fluid circuit comprising a first heat transfer area and a second heat transfer area, each configured for receiving a heat transfer fluid,
wherein the heat transfer fluid circuit is arranged between the first area and the second area such that the first warm section of the first heating device is in heat exchange relation with the first area, the first cold section of the first heating device is in heat exchange relation with the first heat transfer area, the second warm section of the second heating device is in heat exchange relation with the second heat transfer area, and the second cold section of the second heating device is in heat exchange relation with the second area.

9. The arrangement according to claim 1, wherein the dialysis liquid and the second fluid are completely or substantially identical.

10. The arrangement according to claim 1, wherein the arrangement is configured as a reusable unit.

11. The arrangement according to claim 1, wherein the arrangement is configured as a disposable or single-use article.

12. A medical functional device, configured as a disposable blood cassette, comprising:
at least one arrangement according to claim 1.

13. A medical treatment apparatus, configured as one of a blood treatment apparatus, a dialysis apparatus, or an acute dialysis apparatus, comprising:
at least one arrangement according to claim 1 or the medical functional device according to claim 12.

14. A method for at least one of setting or maintaining a temperature of a dialysis liquid, comprising:
at least one of setting or maintaining the temperature of the dialysis liquid using the arrangement according to claim 1.

15. The method according to claim 14 for heating the dialysis liquid, further comprising:
introducing the dialysis liquid into the first area;
heating the dialysis liquid in the first area by the first heating device by transferring heat from the first warm section of the first heating device onto the first area; and
heating the first cold section of the first heating device or a second cold section of a second heating device by transferring heat of a second fluid of the second area onto the first cold section of the first heating device or onto the second cold section of the second heating device.

16. The method according to claim 14 for heating the dialysis liquid, wherein the arrangement further comprises at least one electrically operated second heating device comprising at least one second warm section configured to heat during operation of the second heating device and at least one second cold section configured to cool during operation of the second heating device; wherein the first warm section of the first heating device is in heat exchange relation with the first area, and the second cold section of the second heating device is in heat exchange relation with the second area, the method further comprising:
introducing the dialysis liquid into the first area;
heating the dialysis liquid in the first area by the first heating device by transferring heat from the first warm section of the first heating device onto the first area;
heating the second cold section of the second heating device by transferring heat of a second fluid of the second area onto the second cold section of the second heating device;
using a heat transfer fluid within a heat transfer fluid circuit comprising a first heat transfer area and a second heat transfer area, wherein the heat transfer fluid circuit is arranged between the first area and the second area such that the first warm section of the first heating device is in heat exchange relation with the first area, the first cold section of the first heating device is in heat exchange relation with the first heat transfer area, the second warm section of the second heating device is in heat exchange relation with the second heat transfer area, and the second cold section of the second heating device is in heat exchange relation with the second area;
heating the heat transfer fluid in the second heat transfer area by the second heating device by transferring heat from the second warm section of the second heating device onto the second heat transfer area; and
transferring heat of the heat transfer fluid of the first heat transfer area onto the first cold section of the first heating device.

17. The method according to claim 14 for heating the dialysis liquid, wherein the arrangement is configured for heating the dialysis liquid in a first time interval and configured for cooling the dialysis liquid in a second time interval differing from the first time interval, the method further comprising:
introducing the dialysis liquid into the first area;
heating the dialysis liquid in the first area by the first heating device by transferring heat from the first warm section of the first heating device onto the first area; and
changing a power supply of at least one of the electrically operated first heating device and an electrically operated second heating device such that the dialysis liquid in the first area is cooled by the first heating device by transferring cold from the first warm section of the first heating device onto the first area.

* * * * *